(12) United States Patent
Drevik

(10) Patent No.: US 6,908,456 B1
(45) Date of Patent: Jun. 21, 2005

(54) ABSORBENT ARTICLE WITH MAIN ABSORBING PART IN FRONT PORTION

(75) Inventor: Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 405 days.

(21) Appl. No.: 10/130,424
(22) PCT Filed: Nov. 17, 2000
(86) PCT No.: PCT/SE00/02258
§ 371 (c)(1), (2), (4) Date: Jul. 10, 2002
(87) PCT Pub. No.: WO01/35888
PCT Pub. Date: May 25, 2001

(30) Foreign Application Priority Data

Nov. 18, 1999 (SE) .............................. 99041980

(51) Int. Cl.[7] ................................ A61F 13/15
(52) U.S. Cl. .................... 604/385.04; 604/385.01; 604/385.03; 604/385.101
(58) Field of Search ............... 604/385.01, 385.03, 604/385.04, 386, 385.101, 378

(56) References Cited

U.S. PATENT DOCUMENTS 5,683,373 A * 11/1997 Darby .............. 604/385.01
5,729,835 A    3/1998 Williams

FOREIGN PATENT DOCUMENTS

WO    95/09592    4/1995
WO    97/39713    10/1997

* cited by examiner

Primary Examiner—Jacqueline F. Stephens
(74) Attorney, Agent, or Firm—Burns, Doane, Swecker & Mathis, L.L.P.

(57) ABSTRACT

The invention relates to an absorbent product with a longitudinal direction and a transverse direction, two side edges extending essentially in the longitudinal direction, a front portion, a rear portion, a first surface and a second surface, and an absorption body arranged between the first surface and the second surface. The absorbent product is essentially triangular in shape, the front portion being wider than the rear portion. The absorption body also has a main absorption part which is shaped and positioned in such a manner in the plane of the product that at least 85% of the total absorption capacity of the product is in the front three quarters of the length of the product and at least 70% of the absorption capacity is found in the front half of the product.

8 Claims, 2 Drawing Sheets

ABSORBENT ARTICLE WITH MAIN ABSORBING PART IN FRONT PORTION

TECHNICAL FIELD

The invention relates to an absorbent product such as a sanitary towel, a panty liner or an incontinence pad with a longitudinal direction and a transverse direction, two side edges extending essentially in the longitudinal direction, a front portion, a rear portion, a first surface and a second surface, and an absorption body arranged between the first surface and the second surface, which product is essentially triangular in shape, the front portion being wider than the rear portion.

BACKGROUND ART

Absorbent products such as sanitary towels, panty liners and incontinence pads are intended to be worn in close contact with the body of the wearer. In this connection, such an absorbent product is usually arranged inside the briefs of the wearer and is kept in contact with the body during use by pressure from the briefs. However, it has become much more common for women to wear what are known as thongs, that is to say briefs in which the rear part of the crotch portion is very narrow. In this connection, sanitary towels, panty liners and incontinence pads which are designed to fit in conventional briefs have proved to be virtually impossible to fasten in a thong in such a manner that the towel or the panty liner sits correctly in relation to the body of the wearer and is moreover held in position throughout use. Furthermore, thongs are often worn for aesthetic reasons because they are virtually invisible even under clinging clothes and do not give rise to unsightly edge lines or creases in the clothes. With a conventional absorbent product, which projects beyond the edges of the thong, a large part of the desired aesthetic effect of wearing a thong is of course lost. Absorbent products have therefore been produced, which are adapted to the shape of a thong. Such absorbent products are described in SE 9803981-1, WO 97139713 and SE 9901758-4. However, the special triangular shape with a very narrow rear portion, which is necessary in order that a product can fit in a thong, means that the surface area available for absorption is relatively small. The risk of leakage is then great if the absorption body is not capable of catching and absorbing all the bodily fluid discharged.

One object of the invention is therefore to provide an absorbent product which is suitable for use together with a thong and which affords a high degree of leakproofness. Another object of the invention is to produce an absorbent product which is flexible, comfortable and inconspicuous to wear.

DISCLOSURE OF INVENTION

By means of the present invention, an absorbent product of the type mentioned in the introduction has been produced, which product essentially eliminates the problems mentioned above associated with absorbent products intended for use together with thongs.

A product according to the invention is characterized mainly in that the absorption body has a main absorption part which is essentially plane and is shaped and positioned in such a manner in the plane of the product that at least 85% of the total absorption capacity of the product is in the front three quarters of the length of the product and at least 70% of the absorption capacity is found in the front half of the product.

By concentrating the absorption capacity in a primary liquid absorption area where liquid can be absorbed and stored, it is possible to limit and control the spread of liquid in the absorbent product.

As the product is worn inside a thong, it will, on account of the very special shape of the thong, fit tightly over the genitals and the vaginal orifice of the wearer. It has also been found that the narrow rear portion of the thong presses the product against the body of the wearer, so that a very effective seal is obtained from the perineum backwards. By virtue of the fact that the main absorption part of the product is essentially triangular, absorbed bodily fluid will in the first place be transported forwards, towards the wider part of the main absorption part. As a result, an absorbent product according to the invention has unique leakproofness combined with a high degree of inconspicuousness and comfort.

It is advantageous if the main absorption part consists essentially of a more fine-capillary and/or more hydrophilic material than a surrounding secondary absorption part, or if the main absorption part comprises superabsorbents, because this means that liquid will be transported in the direction from the secondary absorption part to the main absorption part and not in the opposite direction. As a result, the edges of the main absorption part also function as liquid transport barriers, so that liquid will not pass from the main absorption part to the fluffier and/or less hydrophilic secondary absorption part until the main absorption part is saturated with liquid.

It has been found that if the main absorption part is of essentially triangular shape with the wider part arranged in the front portion of the product and the narrower part facing the rear portion of the product, the absorption capacity will be concentrated towards the front portion of the product and the spread of liquid in the product will take place essentially in the forward direction.

According to one embodiment of the invention, the product comprises a secondary absorption part, the secondary absorption part extending outside the main absorption part in the plane of the product, at least within the rear portion of the product, the secondary absorption area accounting for at most 25% of the total absorption capacity of the product. The secondary absorption area constitutes an impediment to leakage of bodily fluid from the edges of the product and moreover serves as a safety zone which can absorb small quantities of liquid which may reach the edge portions of the product and the narrowest part of the rear portion of the product. According to one embodiment, the secondary absorption part comprises portions which completely surround the main absorption part in the plane of the product.

Suitable material for the main absorption part is one or more layers of cellulose fibres with a density of at least 150 g/dm$^3$. In this connection, a particularly suitable material consists of dry-formed cellulose fibres with a density of at least 250 g/dm$^3$.

It has also been found suitable for the secondary absorption part to comprise a layer of bound pulp-based material with a density of at most 125 g/dm$^3$. In this connection, bound material means fibrous material which is bound by a binder which is arranged on one or both surfaces of the material layer, or cellulose fibre layers which contain a proportion of binding fibres which are activated in order to stabilize the fibrous structure. Combinations of different types of binding methods are also possible. The secondary absorption part can be arranged on the first surface of the product and extend over the main absorption part and beyond the edges of the primary absorption area around the entire periphery of the main absorption part, or be arranged only around the periphery of the main absorption part.

In order to avoid accumulation of liquid and in order to counteract leakage in the rear portion of the product, it has been found suitable for the main absorption part to end, in the rear portion of the product, at a distance from the rear edge of the product which constitutes at least 10% of the total length of the product. In this connection, it is suitable for the rearmost part of the rear portion to comprise a soft, compressible material. Such a material serves several functions. For example, it increases the comfort of the product, imparts firmness to the very narrow rear portion, and constitutes a leakage barrier. It may also be suitable for the rearmost part of the rear portion to have a certain capacity to absorb liquid to the extent of individual drops of liquid.

BRIEF DESCRIPTION OF DRAWINGS

The invention is described in greater detail below with reference to the exemplary embodiments shown in the appended drawings, in which.

MODE(S) FOR CARRYING OUT THE INVENTION

Figure 1:
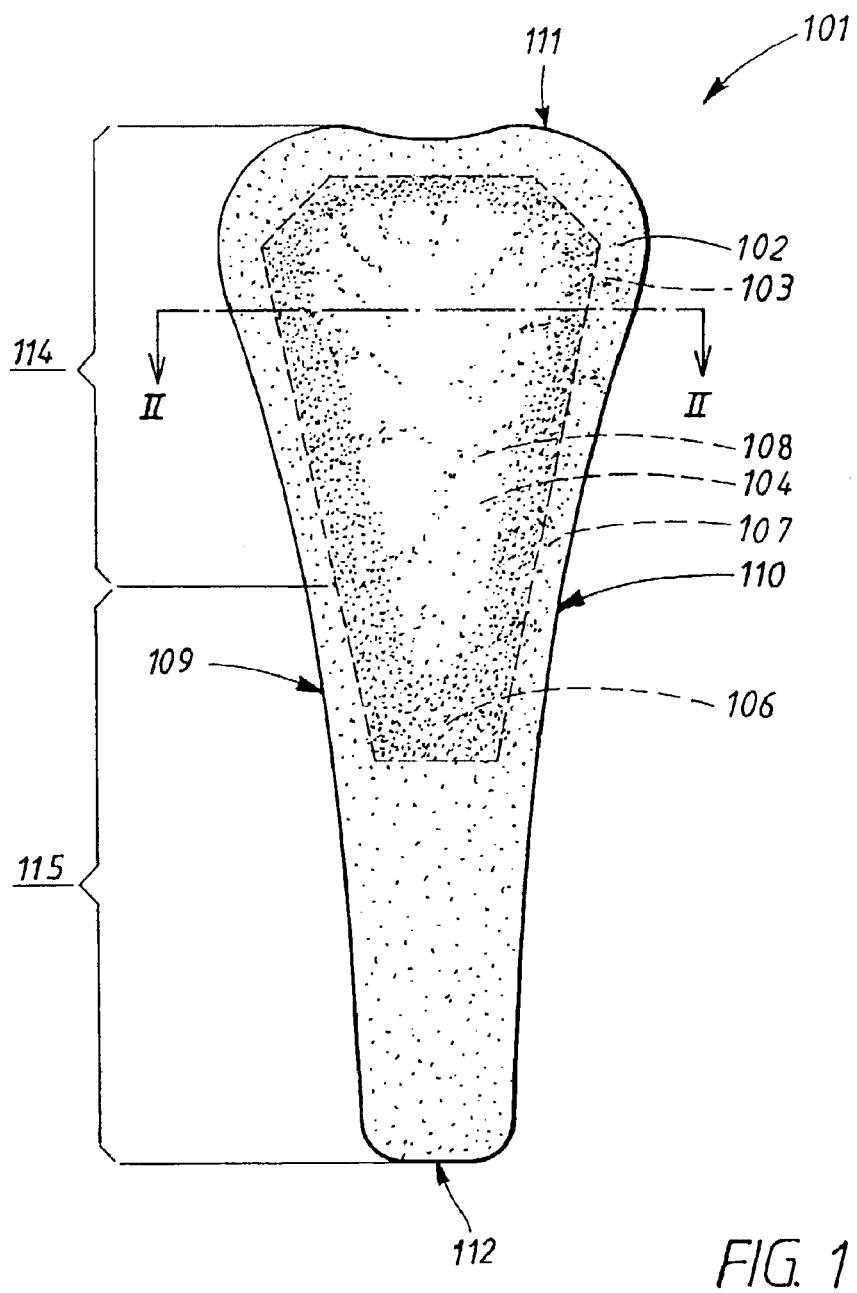
FIG. 1 shows a sanitary towel according to a first embodiment of the invention.
Figure 2:
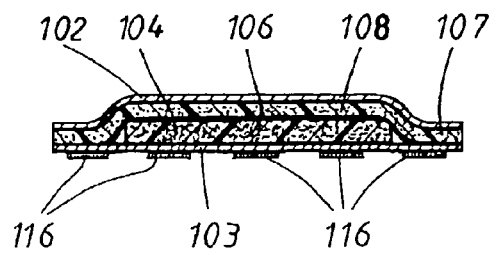
FIG. 2 shows a section along the line II—II through the sanitary towel in FIG. 1.

The sanitary towel 101 shown in FIGS. 1 and 2 comprises a liquid-permeable surface layer 102 arranged on that side of the sanitary towel which is intended to face a wearer during use, a liquidtight rear-side layer 103 arranged on that side of the sanitary towel which is intended to face away from the wearer during use, and an absorption body 104 enclosed between the two surface layers 102, 103.

The liquid-permeable surface layer 102 is the same shape and size as the absorption body 104. The rear-side layer 103 is also shaped like the absorption body. The surface layers 102, 103 are connected to the absorption body 104, for example by gluing, needling, sewing, or by welding using heat or ultrasound.

The liquid-permeable surface layer 102 is of conventional type and can therefore consist of any liquid-permeable material suitable for the purpose. Examples of such material are different types of thin nonwoven material, perforated plastic films, net material, liquid-permeable foam material or the like. The liquid-permeable surface layer 102 can be constructed from two or more different materials in order to provide different functions of the surface layer. For example, it is usual to arrange a liquid-transporting layer inside a liquid-admission layer. It is also known to arrange different types of material on different parts of that surface on the sanitary towel which faces the wearer during use. A material with good admission capacity can therefore advantageously be arranged in that portion of the sanitary towel which is expected to be moistened first by the major part of the bodily fluid, while portions of the surface layer which are in the first instance to constitute a contact surface against the body of the wearer are provided with a material which has been optimized with regard to softness and kindness to the skin.

It is not necessary either for the invention that the liquid-permeable surface layer 102 consists of a separate material layer, but the surface layer 102 can be a surface on the absorption body 104 of the sanitary towel 101.

The liquidtight rear-side layer 103 can also consist of any suitable liquidtight material. Particularly advantageous materials are thin plastic films, liquidtight nonwoven materials, or materials which are coated with liquidtight material such as wax, resin, adhesive or the like. It is also possible to use liquidtight material laminates. It may be desirable, for example, to provide the rear side of the product with an outer layer of a textile nature, for example a nonwoven layer. Such a nonwoven material provides a soft skin-friendly textile surface and affords advantages such as a high degree of wearer comfort, high friction and thus better retention in the thong. Furthermore, a textile surface is often considered to have an aesthetically attractive appearance. It is also an advantage if the liquidtight rear-side layer 103 is breathable, that is to say it allows gas and water vapour to pass through the layer.

It is not necessary for the invention for the surface layers and the absorption body to have the same extent in the plane of the product. It is therefore an alternative possibility to enclose the absorption body in a conventional manner between two surface layers with somewhat greater extent in the plane than the absorption body. In such an embodiment, the surface layers are interconnected within an edge join projecting around the absorption body. Such an edge join can be produced by, for example, gluing, sewing or welding using heat or ultrasound.

The absorption body 104 consists of two parts, a first part which constitutes the main absorption part 106 of the absorption body 104, and a second part which is relatively thin and is in the form of one or more material layers which extend over essentially the entire surface of the sanitary towel. During use of the sanitary towel 101, it is arranged in the genital area of the wearer, with a portion located in the region of the vaginal orifice of the wearer. As a result, discharged bodily fluid will meet the sanitary towel 101 within a limited and to a great extent predetermined area on the sanitary towel, what is known as the wetting area. The positioning of the main absorption part 106 is selected in such a manner that it coincides with the anticipated wetting area of the sanitary towel 101. The main absorption part 106 is therefore considerably smaller in area than the sanitary towel as a whole. By virtue of the fact that the main absorption part 106 is positioned in the wetting area of the sanitary towel, however, essentially all the bodily fluid discharged into the sanitary towel will still pass into and be absorbed in the main absorption part 106. It is therefore of utmost importance that the main absorption part 106 has sufficient absorption capacity to be capable of absorbing the expected quantity of bodily fluid. In this connection, the absorption capacity in the main absorption part 106 should be at least 75%, and preferably at least 85%, of the total absorption capacity of the sanitary towel. It is usually estimated that a panty liner should have an absorption capacity of roughly 3–5 ml and a sanitary towel should be capable of absorbing roughly 12–15 ml. For products intended for night use, for example, or for incontinence pads, an even greater absorption capacity may be desirable.

The main absorption part 106 is of essentially triangular shape and is positioned in such a manner that the wider part, at the base of the triangle, will face the abdomen of the wearer when the sanitary towel is placed inside a thong. This means that liquid meeting the main absorption part 106 will be absorbed towards the front in the sanitary towel, where the greater quantity of absorption material is situated. As a result, liquid is prevented from running towards the rear and leaking out of the sanitary towel.

The second part of the absorption body 104 is arranged as a layer between the liquid-permeable surface layer 102 and the main absorption part 106 and serves as a liquid-transfer layer 108 between the liquid-permeable surface layer 102 and the main absorption part 106. The second part of the absorption body 104 also extends beyond the edges of the main absorption part 106 in the plane of the product, around the entire periphery of the main absorption part 106, and then constitutes a secondary absorption part 107 around the main absorption part 106.

Suitable absorbent materials for use in the absorption body 104 are, for example, cellulose fluff pulp, absorbent bound fibre layers, tissue layers, absorbent foam, peat or the like. The absorption body 104 can also contain superabsorbent polymers, that is to say polymers with the capacity to absorb several times their own weight of liquid, forming a liquid-containing gel. Superabsorbents are usually in the form of particles, flakes, fibres, granules or the like. The superabsorbent material can be used on its own or together with other absorbent material.

The materials in the main absorption part 106 and, respectively, the secondary absorption part 107 are advantageously selected in such a manner that the main absorption part is more fine-capillary and/or has greater hydrophilicity than the secondary absorption part 107. A fine-capillary material can be produced by, for example, compressing a porous, compressible structure, such as a fibre wadding, or by selecting a material with small pores. Generally, it can be said that fibrous structures with a large proportion of thin fibres have finer capillaries than fibrous structures with a large proportion of thick fibres. In a corresponding manner, a difference in hydrophilicity can be obtained either by treating the material chemically or physically or by selecting materials which have different hydrophilicity from the outset.

In order to achieve the desired effect of rapid liquid admission to the main absorption part 106, great absorption capacity and liquid-retaining capacity in the main absorption part 106, as well as little or no spread of absorbed liquid from the main absorption part to the secondary absorption part 107 and the liquid-transfer layer 108, the main absorption part 106 should therefore comprise hydrophilic material with a great absorption capacity, such as cellulose fibres, superabsorbent material or the like, while the material in the secondary absorption part 107 and the liquid-transfer layer 108 can be selected from materials with very low absorption capacity, for example fibre wadding made of synthetic fibres. A material which has been found to function particularly well as absorption material in the main absorption part is the dry-formed cellulose fibrous material described in WO 94/10956. Materials which have proved to function particularly well as secondary absorption material are airy bound cellulose-fibre-based materials with a density of at most 125 g/dm$^3$.

As mentioned, the secondary absorption part 107 surrounds the main absorption part 106 around its entire periphery. As a result, the secondary absorption part 107 forms a safety zone which can catch and absorb small quantities of liquid, or individual drops of liquid, which meet the sanitary towel outside the wetting area. Owing to its low liquid-transport capacity, the secondary absorption part 107 also prevents liquid reaching the edges of the sanitary towel and causing leakage. As the main absorption part 106 has to have a great absorption capacity in relation to its area, this area usually has relatively great rigidity. The secondary absorption part 107 then serves the additional purpose of constituting a soft cushioning between the main absorption part 106 and the body of the wearer.

It may also be suitable to make liquid transport in the plane of the sanitary towel even more difficult by providing the sanitary towel with some form of liquid barrier which prevents liquid being transported in the absorption material or in the liquid-permeable surface layer 102 to the very edges of the sanitary towel. Examples of such liquid barriers are compressions, welds, strands of adhesive, folded-over plastic strips or means of rendering materials hydrophobic, such as wax or the like. In this connection, the liquid barriers can be arranged along the edges of the sanitary towel and/or along the edges on the main absorption part 106.

As can be seen from FIG. 1, the sanitary towel 101 is designed with a relatively wide front portion 114 and a considerably narrower rear portion 115. The sanitary towel 101 also has two side edges 109, 110, the main extent of which is in the longitudinal direction of the sanitary towel, and an essentially transverse front edge 111 and a likewise transverse rear edge 112.

During use of the sanitary towel 101, the front portion 114 is that part of the sanitary towel which faces forwards on the wearer and will then be arranged over the genitals of the wearer. The front portion 114 narrows in the direction towards the rear portion 115 which is considerably narrower than the front portion 114.

In order that the sanitary towel does not extend so far back during use that it is conspicuous when it is worn together with a thong, it is suitable for the rear portion 115 of the sanitary towel to have a length of between 80 mm and 140 mm and for the total length of the sanitary towel not to exceed roughly 260 mm.

In order to fasten the sanitary towel in a pair of briefs, a fastening means 116 is arranged on the outside of the rear-side layer 103 of the sanitary towel. The fastening means 116 is in the form of longitudinal strips of self-adhesive glue. Before use, the fastening means 116 is protected in a conventional manner, for example by being covered by a protective layer of paper or plastic treated with silicone or stamped so as to be easily detachable from the adhesive when the sanitary towel is to be used. The adhesive can of course be arranged in any pattern suitable for the purpose. Other types of fastening means can also be used, such as friction coatings, press-studs, clips, fastening flaps or the like. Another alternative is fastening adhesive which is attached to the body of the wearer. Different types of fastening arrangements can also be combined with one another. It is common, for example, to provide a sanitary towel with both fastening adhesive on the rear-side layer and with fastening flaps.

Although the absorption body 104 in the figures is shown as being constructed from two separate parts, it is possible to make the absorption body 104 from a single absorption layer which is imparted greater hydrophilicity and/or more compact structure within the main absorption part 106. A greater absorption capacity within the main absorption part 106 can also be brought about by means of an accumulation of absorption material within this area and/or addition of superabsorbents.

Figure 3:
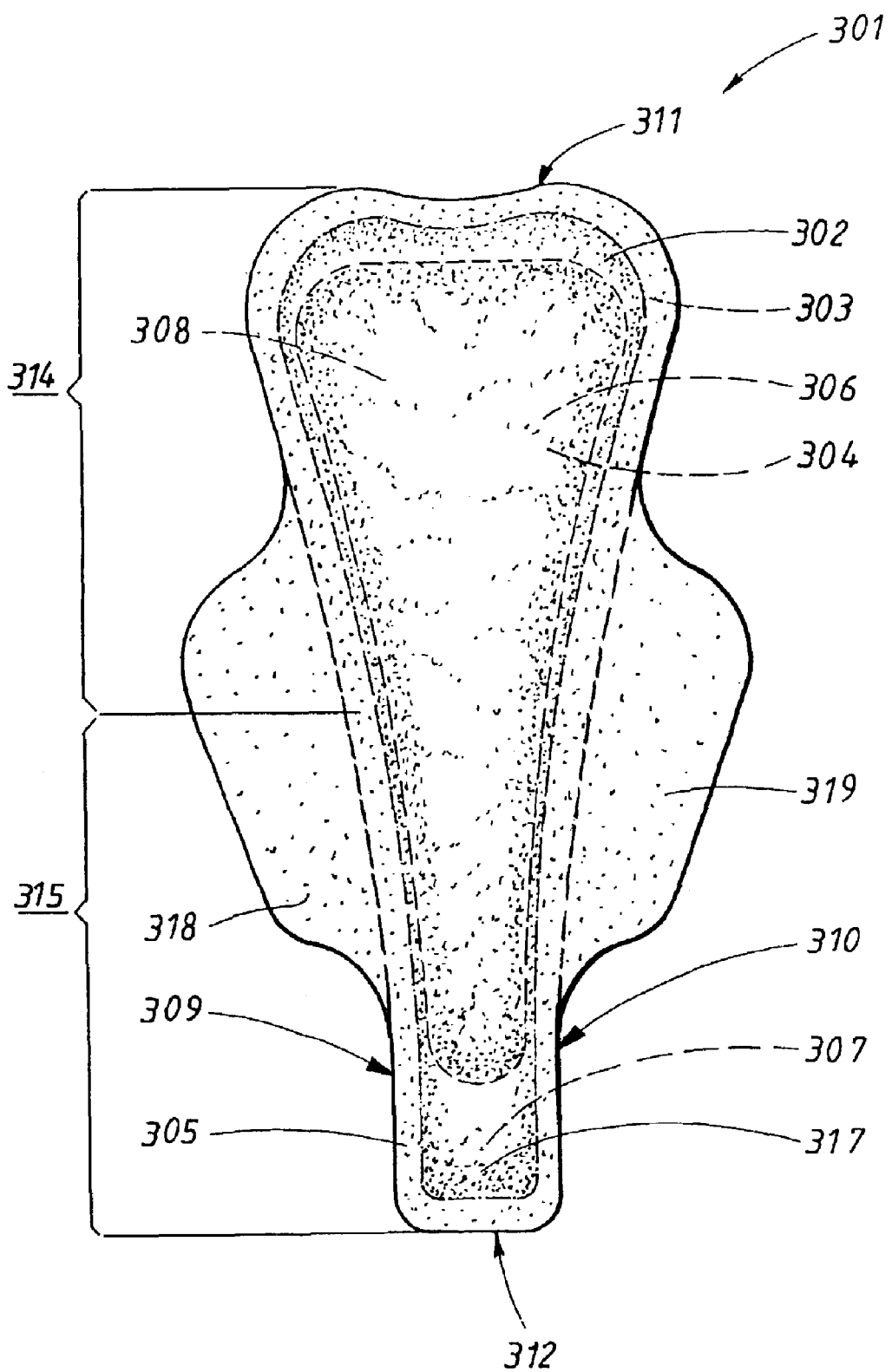
FIG. 3 shows a sanitary towel according to a second embodiment of the invention.

FIG. 3 shows a sanitary towel 301 according to another embodiment of the invention. The sanitary towel 301 shown in FIG. 3 comprises, in a corresponding manner to the sanitary towel 101 in FIGS. 1 and 2, a liquid-permeable surface layer 302 and a liquidtight rear-side layer 303, with an absorption body 304 arranged between the surface layers 302, 303. The surface layers 302, 303 extend out around the periphery of the absorption body 304 in the plane of the sanitary towel 301 and are interconnected within the projecting edge portions 305.

Like the sanitary towel 101 shown in FIGS. 1 and 2, the sanitary towel in FIG. 3 comprises a two-part absorption body 304, an upper layer located immediately inside the liquid-permeable surface layer 302 on the one hand constituting a liquid-transport layer 308 for onward transport of liquid to a main absorption part 306 lying inside and on the other hand forming a secondary absorption part 307 projecting around the edges of the main absorption part 306. The main absorption part 306 is therefore arranged between the upper part 307, 308 of the absorption body 304 and the rear-side layer 303.

The sanitary towel 301 has a wide front portion 314, a considerably narrower rear portion 315, two side edges 309, 310, a front edge 311 and a short rear edge 312. When the sanitary towel is used, it is placed in a pair of briefs with the front portion 314 arranged in the front part of the crotch of the briefs, that is to say the part which the wearer positions towards the front, towards the abdomen, and with the rear portion arranged in the rear part of the crotch of the briefs, that is to say in that part of the briefs which faces backwards, towards the buttocks of the wearer.

As can be seen in FIG. 3, the main absorption part 306 is, broadly speaking, essentially the same shape as the sanitary towel 301. However, the main absorption part 306 does not extend all the way back to the rear edge 312 but ends at a distance from the rear edge 312 which is at least 10% of the total length of the sanitary towel 301. As a result, a small area 317 is formed in the rear part of the rear portion 315, within which area 317 the sanitary towel 301 has extremely low absorption capacity because only the secondary absorption part 307 is present in the rearmost area 317. The secondary absorption material then serves to catch small quantities of liquid which may reach the rear area 317 of the rear portion 315, and constitutes a soft, comfortable part which easily moulds itself to the body of the wearer and does not chafe or otherwise irritate the skin of the wearer. As discussed in connection with the sanitary towel 101 shown in FIGS. 1 and 2, the material in the secondary absorption part 307 should be selected in such a manner that essentially no liquid transfer takes place in the direction from the main absorption part 306 to the secondary absorption part 307, as a result of which the secondary absorption part 307 within the rear area 317 also constitutes a barrier against liquid leakage in the rear portion 315 of the sanitary towel 301.

The sanitary towel 301 shown in FIG. 3 also has fastening flaps 318, 319 which are arranged centrally in the longitudinal direction of the sanitary towel along the side edges 309, 310. The fastening flaps 318, 319 are intended, when the sanitary towel is arranged in a pair of briefs, to be folded around the leg edges of the briefs and fastened to the briefs, or to themselves on the outside of the crotch of the briefs. For this purpose, the fastening flaps 318, 319 are suitably provided with separate fastening means, for example adhesive or a touch and close fastener. Such fastening means are not shown in FIG. 3. It is also possible to use fastening flaps without separate fastening means. It is known, for example, to use fastening flaps which are fastened to the absorbent product with the free part of the flaps already directed in over the rear-side layer from the outset. Such fastening flaps are self-locking and are pressed against the underside of the product when the product is bent in the longitudinal direction, for example when it is arranged in a pair of briefs and then shaped according to the body of the wearer.

Fastening flaps do not of course have to have the shape or size shown in FIG. 3. Other types of fastening flaps can be used instead. It is of course also possible to omit the fastening flaps on the sanitary towel 301 shown in FIG. 3.

The sanitary towel in FIG. 3, like that shown in FIGS. 1 and 2, is also provided with a fastening means arranged on the rear-side layer 303 for fastening the sanitary towel in the briefs of the wearer. The fastening means is not visible in FIG. 3.

Although the invention is described above in connection with sanitary towels, it can of course also be applied to absorbent products such as incontinence pads and panty liners.

What is claimed is:

1. An absorbent product with a longitudinal direction and a transverse direction, two side edges extending essentially in the longitudinal direction, a front portion, a rear portion, a first surface and a second surface, and an absorption body arranged between the first surface and the second surface, which product is essentially triangular in shape, the front portion being wider than the rear portion, wherein the absorption body has a main absorption part which is shaped and positioned in such a manner in a plane of the product that at least 85% of a total absorption capacity of the product is in a front three quarters of a length of the product and at least 70% of the absorption capacity is found in a front half of the product, and wherein the product also comprises a secondary absorption part, the secondary absorption part extending outside the main absorption part in the plane of the product, at least within the rear portion of the product, the secondary absorption area accounting for at most 25% of the total absorption capacity of the product.

2. Absorbent product according to claim 1, wherein the main absorption part is of essentially triangular shape with the wider part arranged in the front portion of the product and the narrower part facing the rear portion of the product.

3. Absorbent product according to claim 1, wherein the secondary absorption part of the product comprises portions which completely surround a primary absorption area in the plane of the product.

4. Absorbent product according to claim 1, wherein the secondary absorption area comprises a layer of bound cellulose-based fibrous material with a density of at most 125 g/dm$^3$.

5. Absorbent product according to claim 4, wherein the secondary absorption part is arranged on the first surface of the product and extends over the main absorption part and beyond the edges of the main absorption part around the entire periphery of the main absorption part.

6. Absorbent product according to claim 1, wherein the main absorption part comprises a layer of cellulose fibres with a density of at least 150 g/dm$^3$.

7. Absorbent product according to claim 6, wherein the main absorption part comprises a layer of dry-formed cellulose fibres with a density of at least 250 g/dm$^3$.

8. Absorbent product according to claim 1, wherein the main absorption part is not present in a part of the rear portion located closest to the rear edge, which corresponds to at least 10% of the total length of the product.

* * * * *